(12) United States Patent
Persichina et al.

(10) Patent No.: US 9,907,689 B2
(45) Date of Patent: Mar. 6, 2018

(54) STOMA PROTECTION GUARD FOR OSTOMY POUCH

(71) Applicants: Michael Thomas Persichina, Rolling Hills Estates, CA (US); Joseph M. Baker, Los Angeles, CA (US)

(72) Inventors: Michael Thomas Persichina, Rolling Hills Estates, CA (US); Joseph M. Baker, Los Angeles, CA (US)

( * ) Notice: Subject to any disclaimer, the term of this patent is extended or adjusted under 35 U.S.C. 154(b) by 40 days.

(21) Appl. No.: 14/937,588

(22) Filed: Nov. 10, 2015

(65) Prior Publication Data

US 2017/0128254 A1 May 11, 2017
US 2017/0281398 A9 Oct. 5, 2017

Related U.S. Application Data

(60) Provisional application No. 62/080,093, filed on Nov. 14, 2014.

(51) Int. Cl.
*A61F 5/44* (2006.01)
*A61F 5/443* (2006.01)

(52) U.S. Cl.
CPC ............ *A61F 5/4404* (2013.01); *A61F 5/443* (2013.01)

(58) Field of Classification Search
CPC ...... A61F 5/4404; A61F 5/4408; A61F 5/445; A61F 5/443; A61F 5/448
See application file for complete search history.

(56) References Cited

U.S. PATENT DOCUMENTS

| 1,922,763 A | 8/1933 | Gricks |
| 4,636,206 A | 1/1987 | Ederati |
| 5,338,315 A | 8/1994 | Baker |
| 5,653,701 A * | 8/1997 | Millman ............... A61F 5/4408 604/337 |
| 6,129,715 A | 10/2000 | Cunningham |
| 8,734,412 B1 * | 5/2014 | Pacelli .................. A61F 5/4404 604/337 |
| 2007/0254129 A1 * | 11/2007 | Horblitt ................... B32B 7/12 428/42.3 |
| 2012/0283678 A1 * | 11/2012 | Nguyen-DeMary .... A61F 5/441 604/337 |
| 2014/0148771 A1 | 5/2014 | Luce |
| 2015/0088081 A1 | 3/2015 | Hakel |

* cited by examiner

*Primary Examiner* — Matthew F Desanto
(74) *Attorney, Agent, or Firm* — Cislo & Thomas, LLP; Katherine B. Sales

(57) ABSTRACT

A stoma guard for ostomy patients that is applied directly to the ostomy pouch. The guard prevents blunt force trauma, helps the user conceal protruded stoma and protects against daily impacts that can harm stoma region. The stoma guard has no sharp corners to prevent leakage and to increase maneuverability. The stoma guard is comprised of a rigid semi circular dome shaped guard and a crescent shaped applicator that secures the guard directly to the ostomy pouch. The guard has a convex shape facing outward that protects the stoma area once secured to the ostomy pouch. The stoma guard is sized to conform around the upper part of the ostomy pouch where the stoma is located. The stoma guard includes an opening at the base permitting flow of waste material. The stoma guard does not need to be removed when emptying waste from the ostomy pouch.

9 Claims, 4 Drawing Sheets

STOMA PROTECTION GUARD FOR OSTOMY POUCH

CROSS-REFERENCE TO RELATED APPLICATIONS

The present application claims benefit of U.S. U.S. Provisional Patent Application No. 62/080,093 titled "Stoma Protection Guard for Ostomy Pouch," filed Nov. 14, 2014, the contents of which are incorporated herein by reference in their entirety.

TECHNICAL FIELD

The present invention relates to methods and devices for protecting surgically created stoma from blunt force trauma and daily impacts to the peristomal region and stoma.

BACKGROUND

Prior Art

The following is a tabulation of some prior art that presently appears relevant:

U.S. Patents

| Patent Number | Kind Code | Issue Date | Patentee |
| --- | --- | --- | --- |
| 1,922,763 | A | 1933 Aug. 15 | Gricks, Rudolph |
| 4,636,206 | A | 1987 Jan. 13 | Ederati, Perez |
| 5,338,315 | A | 1994 16 Aug. | Baker |
| 6,129,715 | A | 2000 Oct. 10 | Cunningham |

U.S. Patent Application Publications

| Publication Nr. | Kind Code | Publ. Date | Applicant |
| --- | --- | --- | --- |
| 20140148771 | A1 | 2014 May 29 | Luce |
| 20150088081 | A1 | 2015 Mar. 24 | Hakel |

Background Art

Ileostomies, urostomies and colostomies, are surgically created openings in which a portion of the intestine is brought through the abdominal wall to form a stoma. A surgically created stoma is generally defined as an opening which connects a portion of a body cavity to the outside environment. Surgical stomas are generally covered or enclosed by a medical appliance or pouch. In the case of an ileostomy, urostomy or colostomy the pouch is secured over the stoma to collect waste from the body. A stoma or ostomy may be temporary or permanent depending on the reason for surgery, i.e., disease, injury, birth defects or cancer. There are many types of pouches available to capture waste from the stoma. The pouch is attached to the skin and located over the stoma. Pouches are made of durable thin plastic designed to collect and secure waste.

The pouch is secured to the stoma by an adhesive barrier that attaches to the skin. Pouch styles and sizes vary from manufacturer to manufacturer but all serve the same purpose, to collect waste.

Ostomy patients or Ostomates, are faced with many problems associated with stomas and stoma collection pouches. One critical problem is trauma due to impacts or pressure on the stoma region, resulting: in injury or discomfort to the stoma located under the ostomy pouch. An impact to the stoma can occur causing pain or discomfort. The ostomy patient can suffer injury or discomfort and have to address the situation. Ostomy pouches are not equipped to protect impacts due to daily activities where objects may bump or hit the stoma unexpectedly. Ostomates experience discomfort due to the lack of security and have worries that their stoma may suffer an impact at any time. Fear of impacts cause many Ostomates to avoid returning to an active everyday lifestyle. Their stoma needs to be protected by more than the thin lining of the ostomy pouch.

Discomfort and impacts to the stoma also causes Ostomates another problem. Ostomates have trouble or the inability to wear form fitting clothing, wear seat belts comfortably or have any amount of pressure around their stoma region. Most surgical stomas are placed near ones waistline, as a result many objects apply pressure over the waistline area. There remains a need for a device to provide unobtrusive protection to the stoma while allowing the person to function a normal active lifestyle.

There are devices in managing protection to the stoma. The proposed devices can be found in U.S. Pat. No. 4,636,206 to Ederati and Perez et al. (1987), U.S. Pat. No. 5,338,315 to Baker et al. (1994), U.S. Pat. No. 1,922,763 to Cricks and Rudolph et al. (1933) and U.S. Patent Applications 20140148771 (2014) Luce, and 20150088081 (2014) Hakel. However, the devices that have been developed require use of hardware, such as a support belts and straps to keep them in position. Unfortunately, the use of additional hardware is very obtrusive, complex and noticeable while wearing. One must use a number of additional hardware to secure these devices. During daily activities this additional hardware can be irritating, bulky and cause an individual discomfort. Application of the current devices are complicated and cumbersome. Further, the current devices can protrude through clothing and are very noticeable. An additional problem with these current devices is that they have to be removed when the ostomy pouch is emptied. This involves the user to remove and re-apply the devices every time they empty their ostomy pouch. An ostomy pouch is already a large addition to the body and the current devices add to the size of the pouch and require additional steps to empty waste from their pouch.

U.S. Pat. No. 6,129,715 to Cunningham (2000), discloses another ostomy protection device using wire cross members that extend over the entire ostomy pouch resulting in a large cumbersome device. The arrangement of wires creates openings in the guard device where objects can impact the stoma. This device also depends on a support strap that has to be attached and detached.

There is need for a device to protect the stoma region located under the ostomy pouch that is discreet and is secured with little to no hardware. A device is needed that does not use support belts or straps. A device is needed that is easy to use, removable, and provides protection to the stoma region. In addition, a device is needed that can remain connected to the ostomy pouch when the user is emptying or adjusting their ostomy pouch.

DESCRIPTION OF EMBODIMENTS

The present embodiment provides methods and devices for the protection of a surgical stoma created for an ileostomy, urostomy or colostomy. The first aspect of the embodiment allows for protection to the stoma region located under the ostomy appliance. Most importantly the embodiment protects against impacts to the stoma that may damage or injure the stoma. This eliminates the fear of impacting the stoma region while wearing the ostomy appliance. In other aspects the embodiment allows for unobtrusive protection giving the Ostomate the ability to carry on with daily activities, wear formfitting clothing and use seat belts comfortably.

In a first embodiment, the present invention comprises a reusable stoma guard for use with an ostomy bag without using support straps or belts, the guard comprising: a body configured to cover and protect a stoma, the body comprising a perimeter; a flange coupled to and extending from at least a portion of the perimeter of the body, the flange having an inner surface; a first connecting adapter having a front surface and a rear surface, the front surface of the first connecting adapter comprising an adhesive material for coupling to the inner surface of the flange; and a second connecting adapter having a front surface and a rear surface, the rear surface of the second connecting adapter comprising an adhesive backing for coupling to a ostomy bag; wherein the rear surface of the first connecting adapter and the front surface of the second connecting adapter are configured for removeably coupling to each other such that the body of the stoma guard is reusable.

In a second embodiment, the present invention comprises a reusable stoma guard for use with an ostomy bag without using support straps or belts, the guard comprising: a dome shape body configured to cover and protect a stoma, the body comprising a perimeter; and a flange coupled to and extending from at least a portion of the perimeter of the body, the flange having an inner surface configured to removeably couple to the ostomy bag such that the stoma guard is reusable. The stoma guard can further comprise a first connecting adapter having a front surface and a rear surface, the front surface of the first connecting adapter comprising an adhesive material for coupling to the inner surface of the flange, and a second connecting adapter having a front surface and a rear surface, the rear surface of the second connecting adapter comprising an adhesive backing for coupling to a ostomy bag, wherein the rear surface of the first connecting adapter and the front surface of the second connecting adapter are configured for removeably coupling to each other and the body of the stoma guard can be re-used.

In a third embodiment, the present invention comprises a stoma guard system comprising: an ostomy bag; and a stoma guard coupled to the ostomy bag without using support straps or belts, the stoma guard comprising: a body configured to cover and protect a stoma; a flange coupled to the body, the flange having an inner surface; a first connecting adapter having a front surface and a rear surface, the front surface of the first connecting adapter comprising an adhesive material for coupling to the inner surface of the flange; and a second connecting adapter having a front surface and a rear surface, the rear surface of the second connecting adapter comprising an adhesive backing for coupling to a ostomy bag; wherein the rear surface of the first connecting adapter and the front surface of the second connecting adapter are configured for removeably coupling to each other and the body of the stoma guard is reusable.

In a fourth embodiment, the present invention comprises a method of installing a stoma guard without using support straps or belts, the method comprising the steps of: coupling an ostomy bag to a stoma; providing the stoma guard; coupling the first connecting adapter to the body; coupling the second connecting adapter to the ostomy bag; and installing the stoma guard by coupling the first connecting adapter to the second connecting adapter.

In all embodiments, the body can be dome shaped and the flange can be slightly curved to contour to the body. Additionally, the first connecting adapter and the second connecting adapter can be crescent shaped. Optionally, the rear surface of the first connecting adapter comprises a hook-material and the front surface of the second connecting adapter comprises a loop-material.

The embodiment guard also gives the user the ability to empty their ostomy pouch without having to remove the embodiment from their pouch. Since the embodiment guard is attached directly to the ostomy pouch there is no need to remove any support belts or straps when removing the ostomy pouch to empty waste.

The embodiment is complementary to the ostomy pouch, providing protection to the stoma that the ostomy pouch does not provide. The device comprises a rigid domed guard for the protection of the stoma and is secured directly to the ostomy appliance using an adhesive applicator that secures the embodiment guard directly to the ostomy pouch. I contemplate the guard embodiment be made using plastic or different materials that can be formed by a tool. The device includes an adhesive applicator that secures it to the ostomy appliance. I contemplate the applicator to be adhesive hook-and-loop material. The guard embodiment can be applied with the adhesive applicator and then attached to the pouch. However, it can use different material used to secure the guard to the ostomy pouch such as adhesive tape, a gasket, plastic adapter, etc. . . . The embodiment is made up of the guard and the applicator. This device is secured directly on top of the ostomy pouch over the stoma to protect the stoma region.

The embodiment is circular shaped dome that is applied to the outside of the pouch fitting around the stoma which is located behind the pouch. The embodiment has a convex shape dome that creates a buffer around the stoma protecting it from impacts. The embodiment is sized to fit around the stoma area and has an opening at the base for the release of waste coming out of the stoma and into the pouch. The embodiment does not use any support belts, strap or additional hardware to secure it to the ostomy appliance. The embodiment is secured directly to the ostomy appliance using the adhesive applicator. At any time, the embodiment can be removed by detaching it from the pouch. The embodiment can be repositioned or reused over and over again.

The size of the embodiment is presently 3.5 inches. However, it can be different sizes depending on the size of the stoma. A stoma does not vary drastically in size. Once the embodiment is applied to the ostomy pouch it can be removed or repositioned at any time. The embodiment will not slip out of position since it secured directly to the ostomy pouch. Since the embodiment does not use belts, straps or other hardware this gives the user much more comfort and protection. The embodiment will not slip out of place or add unnecessary material that may be cumbersome.

The above description and other features of the embodiment will be a described in the following the detailed description, drawings, and appended claims.

BRIEF DESCRIPTION OF THE DRAWINGS

In the drawings, closely related figures are numbered with reference numbers.

Figure 1:
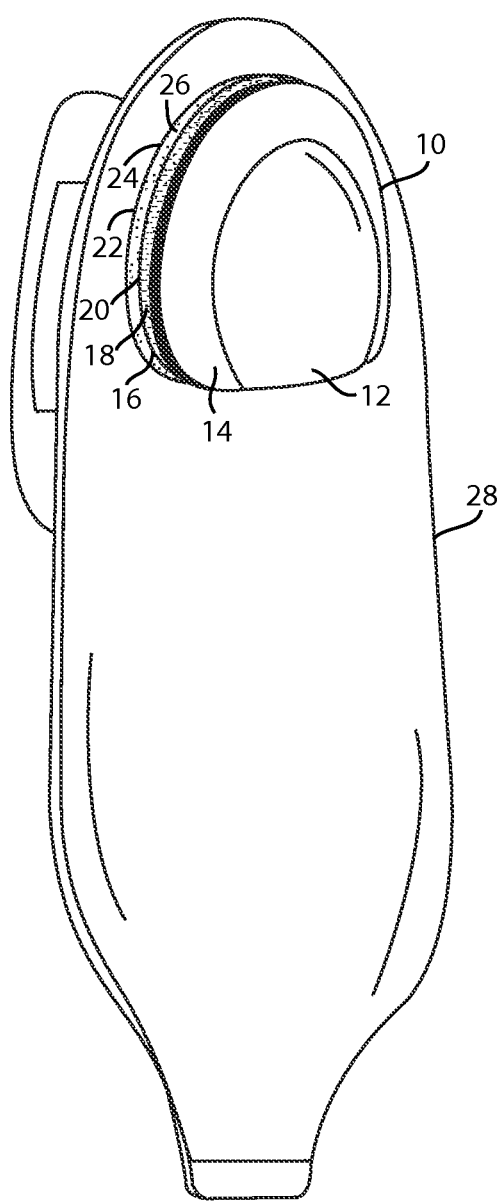
FIG. 1 shows a perspective view of the embodiment of the ostomy guard attached to an ostomy pouch.

DRAWINGS—REFERENCE NUMERALS 10 embodiment of an ostomy guard
12 dome shape part of embodiment
14 flange part of embodiment
16 connecting adapter
18 adhesive backing
20 hook-material
22 connecting adapter
24 adhesive backing
26 loop-material
28 ostomy pouch
30 stoma

DETAILED DESCRIPTION OF SPECIFIC EMBODIMENTS

FIG. 1 (perspective view) is an embodiment of the stoma guard 10 for protecting a stoma is shown attached to an ostomy pouch 28. The device 10, includes connecting adapters 16 and 22, configured for providing protection of the stoma located behind the ostomy pouch 28, where the ostomy pouch 28 attaches to the individual. The device 10, is supported and attached to the ostomy pouch 28, using the connecting adapters 16 and 22.

Figure 2:
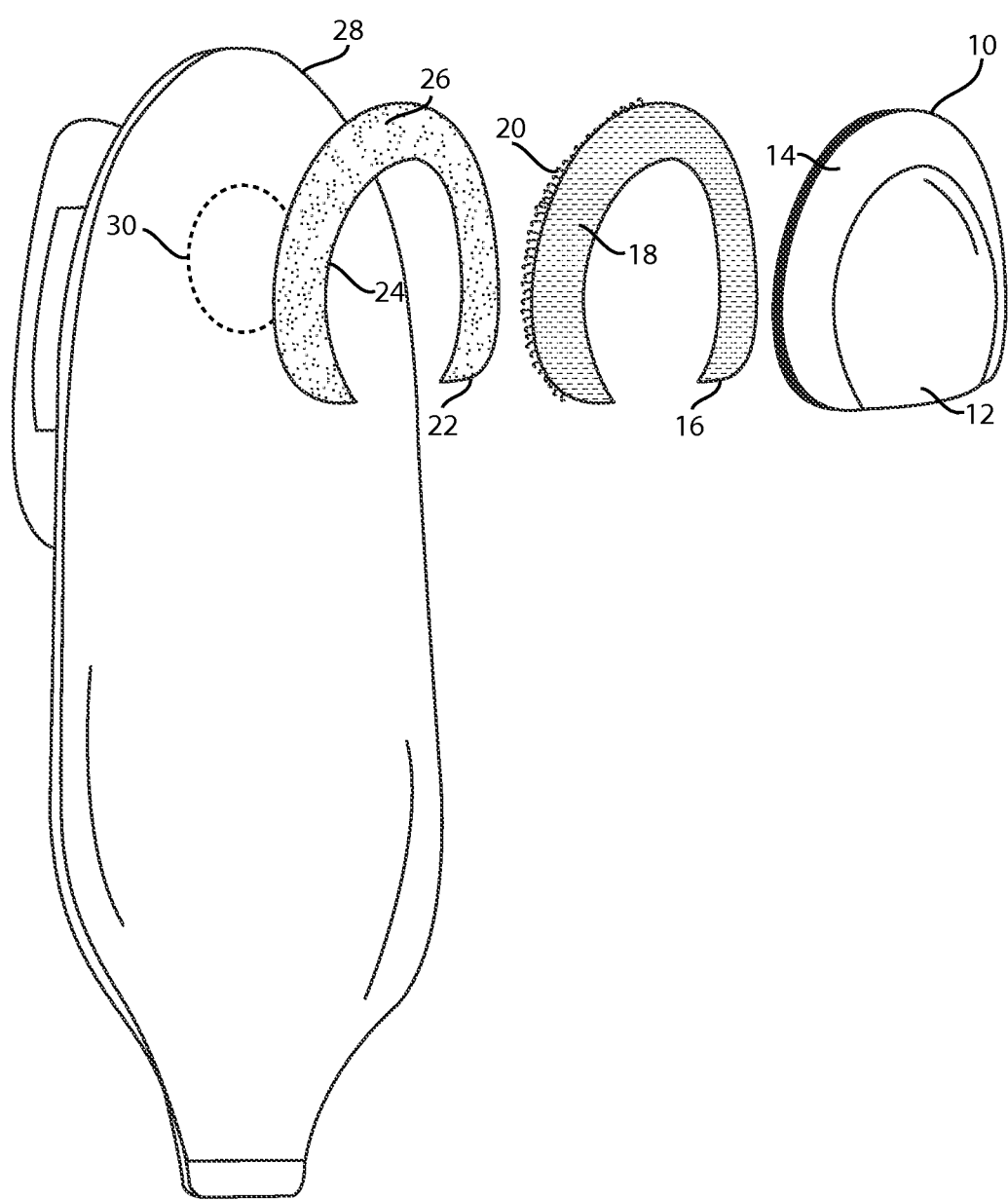
FIG. 2 shows an exploded perspective view in more detail of the embodiment shown in FIG. 1.

In greater detail, referring to FIG. 2 (exploded perspective view), the ostomy guard 10 is suitable in size and shape for protecting the stoma 30. The device 10 includes connecting adapters 16 and 22 used to attach it to the ostomy pouch 28. The adapter 16, is attached to the device 10, using an adhesive material 18. The adapter 22, is attached to the ostomy pouch 28, using an adhesive material 24. Once the connecting adapter 16 is secured to the device 10, using adhesive backing 18, and the connecting adapter 22 is secured to the ostomy pouch 28; the two adapters 16 and 22 can support the device 10, using a hook-material 20 and loop-material 26 support system. The hook-material 20 and loop-material 26 support system can be removed and reapplied at any time while the connecting adapter 16 remains secure to the device 10 and the connecting adapter 22 remains secure to ostomy pouch 28. Once device 10, and connecting adapters 16 and 18 are secured to the ostomy pouch 28 using adhesive backing 18 and 24, the device 10 can be worn as a protective guard.

Figure 3:
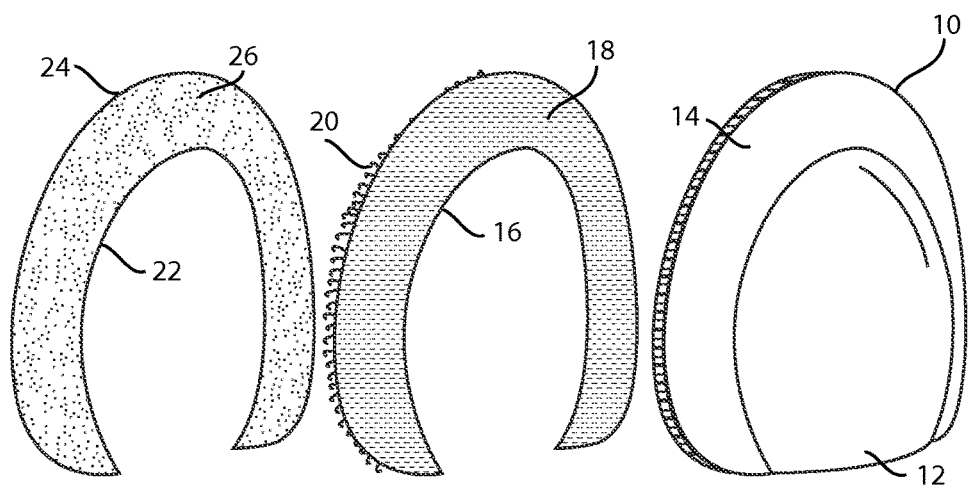
FIG. 3 shows a perspective view of the embodiment and its adhesive adapter parts.

FIG. 3 is a front view of the embodiment shown in FIGS. 1 and 2. FIG. 3 shows a more detailed view of the embodiment of a guard 10; which has a dome shape 12, and a flange 14 that comprises the guard 10. The dome shape 12 extends outward protecting the stoma. The flange 14, is slightly curved to contour to the body and designed so the connecting adapter 16 and adhesive backing 18 can be secured to the device 10. The connecting adapter 16 has hook-material 20 on one side, the other connecting adapter 22 has loop-material 26. These two adapter materials hook 20 and loop 26 support each other and are used to attached the device 10 to the ostomy pouch 28.

Figure 4:
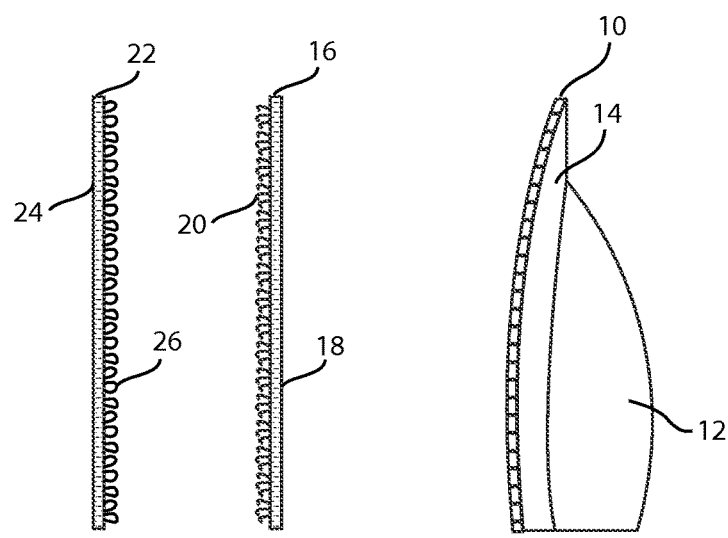
FIG. 4 shows a side view of the device and its adhesive adapter parts.

FIG. 4 is a side view of the embodiment shown in FIG. 3. This is a more detail illustration of how the device 10 and the commenting adapters 16 and 22 fit together.

Figure 5:
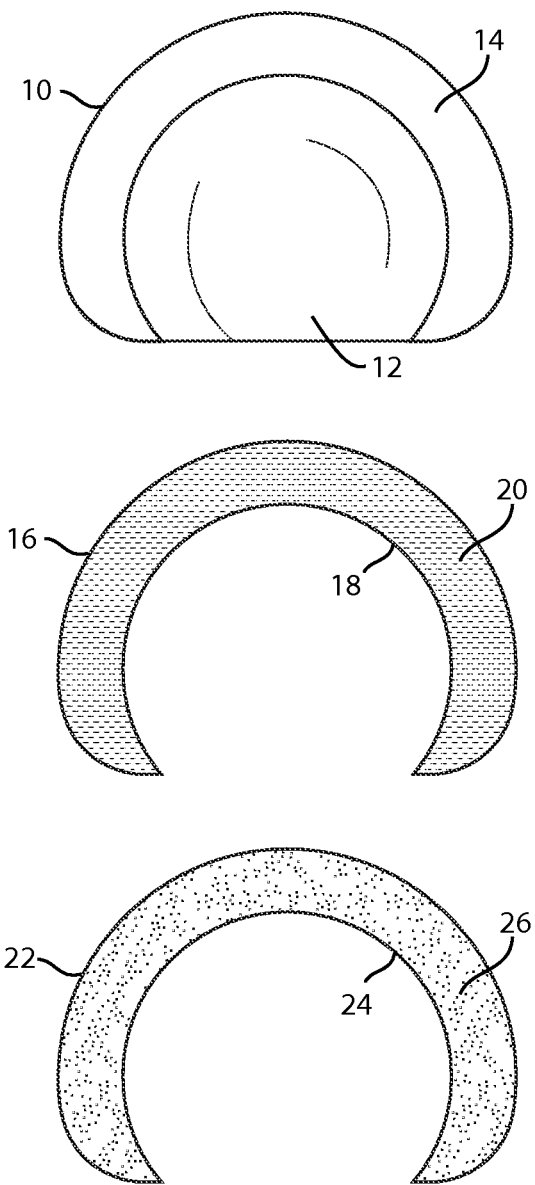
FIG. 5 shows a front view of the embodiment and its adhesive adapter parts.

FIG. 5 is a front view of the embodiment device 10 and its connecting adapters 16 and 22. This illustration shows the general shape of the device 10 and the adapters 16 and 22. The device 10 is shaped with round corners Operations—FIGS. 1, 2, 3, 4, 5

The manner of using the embodiment 10, shown in FIGS. 1 through 5 can be used by an individual. First one must attach the connecting adapter 16 to the device 10, using the adhesive material 18, which is attached to the flange 14 located on the device 10. The connecting adapter 16 is permanently fixed to the flange 14. Next the connecting adapter 22 is secured to the ostomy pouch using adhesive backing 24 on connecting adapter 22. Once the connecting adapter 22 is in place and fitted around the stoma 30, the connecting adapter 22 is permanently fixed to the ostomy pouch 28. Now the device 10 is ready to be used by an individual.

The individual can now attach the embodiment device 10 to protect their stoma 30, located behind the ostomy pouch 28. Since the connecting adapter 16, has hook-material 20, and connecting adapter 22 has loop-material 26, these two hook-material 20 and loop-material 26 support each other by simple pressing them together. The individual can now attach the device 10 to the pouch 28 using the connecting adapters 16 and 22 using the hook-material 20 and loop-material 26. The device 10 is attached by pressing the device 10 which now has hook-material 20, onto the connecting adapter 22 that is secured to the ostomy pouch 28 and the loop-material 26 supports the device 10. At any time, the individual can remove the device 10 from the ostomy pouch 28 by pulling the device 10, separating it from the hook-material 20 and loop-material 26 system.

CONCLUSION, RAMIFICATIONS, AND SCOPE

While the above description contains many specificities, these should not be construed as limitations on the scope, but rather as an exemplification of one or several embodiments. Many other variations are possible. For example, the size of the device can change depending on the size of the individual's stoma, the adapter used to secure the device to the ostomy pouch is not limited to the connecting adapter described, but at the present time the described connecting adapter is preferred. The device can be secured with other material, adhesive or additional fabricated devices. The device can be made of different material, color and shape.

Accordingly, the scope should be determined not by the embodiments illustrated, but by the appended claims and their legal equivalents.

We claim:

1. A method of using a stoma guard without utilizing support straps or belt to secure the stoma guard, the method comprising the steps of:
    a) providing an ostomy bag with a stoma cavity, a first side and second side;
    b) coupling a first connecting adapter to the stoma guard;
    c) before or after step b) coupling a second connecting adapter to an upper part of an outer surface of the second side of the ostomy bag;
    d) attaching the first side of the ostomy bag to a patient;
    e) installing the stoma guard over the stoma cavity of the ostomy bag by coupling the first connecting adapter to the second connecting adapter;

f) completely removing the stoma guard from the ostomy bag by uncoupling the first connecting adapter from the second connecting adapter; and g) re-attaching the first and second connecting adapter, so that the stoma guard can be repositioned or reused.

2. The method of claim 1, wherein the stoma guard comprises:

a) a dome shape body configured to cover and protect the stoma, the body comprising a perimeter; and b) a flange coupled to and extending from at least a portion of the perimeter of the body, the flange having an inner surface configured to removeably couple to the ostomy bag such that the stoma guard is reusable;

wherein the first connecting adapter of step a) couples to the flange of the stoma guard.

3. The method of claim 2, wherein the flange is slightly curved to contour to a users' body.

4. The method of claim 1, wherein the first connecting adapter of step a) has a front surface and a rear surface, the front surface of the first connecting adapter comprising an adhesive material for coupling to the stoma guard.

5. The method of claim 4, wherein the rear surface of the first connecting adapter comprises a hook-material.

6. The method of claim 1, wherein the second connecting adapter of step b) has a front surface and a rear surface, the rear surface of the second connecting adapter comprising an adhesive backing for coupling to the ostomy bag, wherein the rear surface of the first connecting adapter and the front surface of the second connecting adapter are configured for completely removeably coupling to each other, and the body of the stoma guard can be re-used.

7. The method of claim 6, wherein the front surface of the second connecting adapter comprises a loop-material.

8. The method of claim 1, wherein the first connecting adapter of step a) is crescent shaped.

9. The method of claim 1, wherein the second connecting adapter of step b) is crescent shaped.

* * * * *